United States Patent
Seitz

(10) Patent No.: US 9,222,897 B2
(45) Date of Patent: Dec. 29, 2015

(54) METHOD FOR CHARACTERIZING A FEATURE ON A MASK AND DEVICE FOR CARRYING OUT THE METHOD

(75) Inventor: Holger Seitz, Jena (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 1061 days.

(21) Appl. No.: 13/247,579

(22) Filed: Sep. 28, 2011

(65) Prior Publication Data
US 2012/0075456 A1    Mar. 29, 2012

Related U.S. Application Data

(60) Provisional application No. 61/387,514, filed on Sep. 29, 2010.

(30) Foreign Application Priority Data

Sep. 29, 2010   (DE) .................... 10 2010 047 050

(51) Int. Cl.
| H04N 7/18 | (2006.01) |
| G01N 21/956 | (2006.01) |
| G01B 11/02 | (2006.01) |
| G03F 1/84 | (2012.01) |

(52) U.S. Cl.
CPC .......... *G01N 21/95607* (2013.01); *G01B 11/02* (2013.01); *G03F 1/84* (2013.01); *G01N 2021/95676* (2013.01)

(58) Field of Classification Search
CPC .............. G01N 21/95607; G01N 2021/95676; G01B 11/02; G03F 1/84

USPC .............. 348/79; 356/237.4; 355/71; 438/14; 716/21

See application file for complete search history.

(56) References Cited

U.S. PATENT DOCUMENTS

| 2003/0215964 A1* | 11/2003 | Gau et al. ................ 438/14 |
| 2004/0133872 A1* | 7/2004 | Fukuhara et al. ......... 716/21 |
| 2008/0094600 A1* | 4/2008 | Freimann .................. 355/71 |
| 2008/0204735 A1* | 8/2008 | Heiden .................. 356/237.4 |
| 2010/0104128 A1 | 4/2010 | Arnz et al. ................ 382/100 |
| 2011/0090329 A1 | 4/2011 | Poortinga et al. ......... 348/79 |
| 2011/0188732 A1 | 8/2011 | Stroessner ............... 382/144 |

FOREIGN PATENT DOCUMENTS

| DE | 102004033603 | 2/2006 | ............ G01M 11/00 |
| DE | 102006059431 | 6/2008 | .............. G03F 7/20 |
| DE | 102008019341 | 10/2009 | ............ G01M 11/00 |
| DE | 102008049365 | 4/2010 | ............ G02B 21/06 |
| DE | 102009038558 | 3/2011 | .............. G03F 7/20 |
| DE | 102009041405 | 3/2011 | ............ G02B 21/06 |
| WO | 03/096356 | 11/2003 | |
| WO | 2009/083606 | 7/2009 | .............. G03F 7/20 |

\* cited by examiner

*Primary Examiner* — Allen Wong
(74) *Attorney, Agent, or Firm* — Fish & Richardson P.C.

(57) ABSTRACT

A mask inspection microscope is provided for characterizing a mask having a feature. The mask inspection microscope is configured to generate an aerial image of at least one segment of the feature of the mask, acquire a spatially resolved intensity distribution of the aerial image, and determine a total intensity from the intensities of at least one region of the aerial image.

27 Claims, 4 Drawing Sheets

METHOD FOR CHARACTERIZING A FEATURE ON A MASK AND DEVICE FOR CARRYING OUT THE METHOD

CROSS REFERENCE TO RELATED APPLICATIONS

Pursuant to 35 U.S.C. §119, this application claims the benefit of U.S. provisional application 61/387,514, filed on Sep. 29, 2010, and German application DE 10 2010 047 050.3, filed on Sep. 29, 2010, both of which are incorporated by reference.

BACKGROUND OF THE INVENTION

This subject matter is generally directed to a method and a mask inspection microscope for characterizing a feature on a mask.

In the fabrication of semiconductor components, numerous measurement methods are used to monitor the results of the individual steps in the lithographic process.

To verify a process for generating features on wafers, it is advantageous to characterize the smallest features that can still be formed on a wafer. These are referred to as the critical dimension, abbreviated CD. The critical dimension of a feature usually refers to the line width of a feature composed of alternating lines and spaces. In the lithographic process, this feature is first formed on a mask (photomask, reticle), for example as chromium on quartz glass. There are also other known masks, for example phase shift masks (PSM) or reflective masks, that are used particularly with short-wavelength illuminating radiation in the EUV range. By exposure in a scanner, this feature is imaged onto a wafer coated with resist. The desired feature is produced on the wafer by subsequent developing and etching.

The characterization of a feature, particularly the CD or line width of a feature, can be performed both on the mask and on the wafer. Although on-wafer measurement yields very meaningful data, since the product is characterized at the end of the process chain, it is very involved, since the entire wafer exposure process has to be performed for the test.

If the characterization of a feature to be fabricated is performed on the mask itself, errors caused by the behavior of the mask during imaging and by other method steps are not incorporated into the measurement. Errors on the mask are usually intensified by the scanner during imaging. Another problem is that the mask features are known and are optimized by resolution enhancement technology (RET), and thus do not completely match the features that are to be imaged. This makes it difficult, for example, to measure the CD directly on the mask.

Both on mask and on wafer, CD measurement is performed by, for example, scanning electron microscopy (CD-SEM, critical dimension scanning electron microscopy).

Another way to measure the CD is to analyze the aerial images of masks with a mask inspection microscope. In this method, the aerial image shows most of the features that are also being projected onto the wafer.

Another way to characterize masks, such as by measuring the CD of masks and wafers, is afforded by non-imaging optical methods. In the case of transmissive masks, one notable method is to measure the transmission of structured regions of a mask, as disclosed, for example, in International Laid-Open Patent Application WO2009083606A1.

Non-imaging optical methods yield measurement values that are correlated with quality-related properties of the mask, for example the line width or CD of a mask. Masks can be characterized by measuring these values alone. By calibrating the method, it even becomes possible to determine absolute values.

SUMMARY

In one aspect, in general, the invention provides a fast and inexpensive method with a high precision of measurement and a device for characterizing a feature on a mask. A method for characterizing a mask having a feature includes generating an aerial image of the mask; acquiring a spatially resolved intensity distribution of the aerial image; and determining a total intensity from the intensities of at least one region of the aerial image.

The method has the advantage that a characteristic value can be determined quickly and easily from the intensity values of a captured aerial image. The acquisition of the aerial image is simplified, since it is not necessary for the image to be taken in the best focal plane. The focus tolerance range is greater here than the normally specified depth of field. The tolerance range can be, for example, two, three or four times the depth of field.

Implementations of the method can include one or more of the following features. A mask inspection microscope can be used to generate and capture the aerial image. To generate an aerial image, the mask is illuminated with illuminating radiation, for example with light at a wavelength of 193 nm or 13.5 nm. The aerial image is taken in transmission or in reflection. An aerial image can be taken of a segment of the surface of the mask at a specified position. The position is indicated by a characteristic point of the segment or region, for example its center. By configuring illumination settings such as, for example, dipole, quadrupole or annular, and configuring the polarization of the illuminating radiation, conditions can be created that largely match the conditions in the scanner during the actual use of the mask. This makes it possible to achieve meaningful characterization of the mask. For focusing with a mask inspection microscope, either the mask or the objective lens can be moved in the direction of the optical axis of the microscope. The tolerance range for this movement is given by the depth of field. If the depth of field for a given illumination setting in the plane of the mask is, for example, 1 µm, then the tolerance range for focusing in the mask plane is, for example, 2, 3 or 4 µm. These leads to another advantage: once the mask has been oriented a single time in a mask inspection microscope, no focusing is necessary between measurements. This makes the method much faster to carry out.

The spatially resolved intensity distribution of an aerial image can be acquired by a suitable detector disposed in the plane of the aerial image. This detector comprises, for example, a two-dimensional matrix of individual sensors (for example, a CCD sensor composed of a matrix of individual pixels). The individual sensors determine the intensities at the location concerned, i.e., the intensities of the individual pixels.

The total intensity can be calculated by adding the individual intensities together. The total intensity is determined from the intensities of a region of the aerial image. This region can include the entire aerial image. The region can also include only a portion of the aerial image. The total intensity can also be determined from more than one region. A separate total intensity can be determined for each region, or a total intensity can be determined from the intensity values of all the regions. However, if the aerial image contains image artifacts—i.e., regions whose intensities should not be taken into account in determining the total intensity—it is advantageous to choose a suitable region of the aerial image.

In some examples, the total intensity can be normalized to a reference value, particularly to the total intensity measured on a featureless mask. This has the advantage of making it possible to compare the total intensities determined in different series of measurements and also from different masks.

Because the illuminating radiation of a practical measuring device is subject to variations, normalization makes it possible to compare the total intensities obtained in measurements performed at different times.

To effect normalization, all the determined total intensities are referred to a reference value. To normalize the measurement values, the quotients of the measurement values and the reference values are determined. Suitable reference values are total intensities, which can readily be determined in reproducible fashion. For example, the total intensity of a featureless mask can be used as a reference value. As another example, the total intensity without a mask in the imaging beam path can be used as a reference value.

In some examples, the method includes determining a line width of the feature from a correlation between at least one determined total intensity of a feature and a known line width of that feature. This has the advantage that absolute values of the line width of a feature can be obtained in a simple manner from total intensity measurements.

Calibration of the total intensities can be performed against absolute values of the line width of the feature on the mask or on the wafer, or against the line width of the feature in a simulated aerial image. The absolute values can be determined by electron microscopic methods.

In some examples, the method includes predefining at least one position on the mask at which the mask will be characterized.

Various strategies are provided according to the invention for selecting the positions on the mask at which the mask is to be characterized.

The total intensities can be determined at different times at positions on a mask that have been specified once and stay the same. This makes it possible to check whether the quality of the mask is deteriorating, for example due to contamination. The total intensities at the same specified positions can also be determined on different copies of masks having the same feature, thus permitting comparison of the masks.

Comparable features can be selected for purposes of mask characterization. One example of comparable features is features composed of lines and spaces and having the same nominal grating period and line width. In this example, a deviation of the total intensities determined at different positions on a mask or at the same position on different masks would indicate a deviation of the line width or the grating period. Since the grating period in masks can be considered constant in good approximation, comparing the total intensities provides a good measure of how the line widths compare.

In some examples, a plurality of positions distributed evenly over the surface of the mask are predefined. This has the advantage that masks can be characterized even when available information on the features is nonexistent or incomplete. This embodiment is advantageous particularly in combination with the other embodiments for analyzing the aerial images to locate comparable features. This embodiment is also advantageous for comparing different copies of masks having the same feature or comparing the condition of a mask at different times.

In some examples, positions on the mask are determined at which comparable features are formed on the mask. This has the advantage that comparable features can be selected in a targeted manner. Unnecessary measurements and the selection of comparable features from a large number of acquired images can be avoided. The positions can, in particular, be specified on the basis of the mask design.

In some examples, the method includes analyzing the aerial images to identify positions having comparable features. This has the advantage that comparable features can be identified even without knowledge of the mask design.

The analysis of the aerial images can be performed, for example, by frequency analysis, i.e., determination and analysis of the spatial frequency spectra.

A further criterion for selecting positions with comparable features is to predefine an interval for the total intensities. For instance, all positions whose total intensities deviate from each other within predefined limits are taken as comparable features.

In some examples, the method includes determining at least one of the following factors on the basis of the aerial images: grating constant, orientation of the grating, line width, and image error. This has the advantage that comparable features can be identified via selection based on the determined factors. The analysis can be performed on the basis of the spatial frequency spectra of the aerial images or by analyzing the aerial images themselves. For example, positions can be identified at which the grating periods or line widths are identical or are within a predefined tolerance range. These positions can then be taken as comparable features.

If the aerial images contain image artifacts, i.e., subregions having non-comparable structures, then these can also be detected.

In analyzing the spatial frequency spectra of the aerial images, the locations and spacing of the spatial frequency maxima are analyzed, as explained in greater detail in the exemplary embodiments.

In some examples, an exact position is determined by comparing at least one region of the captured aerial image to a simulated aerial image. This has the advantage of increasing the reproducibility of the measurements.

When the mask is being positioned, for example in a mask inspection microscope, the segment of the aerial image that lies in the beam path of the mask inspection microscope can be specified. Should an error occur during subsequent repositioning of the mask, the segments and thus the determined total intensities will deviate from each other. To prevent this and to increase the precision of the positioning, an image simulated on the basis of the mask design can be created in the region of the target position. The position of the measured aerial image can then be corrected by overlaying with the simulated aerial image. A position correction can also be made by overlaying with an aerial image taken with a mask inspection microscope and used as the reference image. A prerequisite here is that the positions of the reference image must agree with the mask design or that any deviations must be known.

In some examples, a direct total intensity is determined by acquiring an individual intensity by means of a high-sensitivity non-imaging sensor. This has the advantage of making it possible to determine a total intensity with high precision by an additional measurement method. The region in this case includes the entire aerial image.

The parallel use of two sensors makes high-precision characterization possible. The high-sensitivity non-imaging sensor can be used to perform high-precision measurement of the direct total intensities. With measurement by the transillumination method, the direct total intensity corresponds in good approximation to the transmission of the mask; for measurement in reflection, it corresponds in good approximation to the reflectance of the mask. These values are comparable to the values for the total intensity of an aerial image that are determined from individual intensities. The measurement results can be correlated with the analysis of the aerial images, and thus with the total intensities determined on the basis of the aerial images.

Time variations of the total intensities can be logged and used to compensate for measurement errors caused by variations in the intensity of the illuminating radiation.

Measurements of total intensities and of direct total intensities can also be performed independently of each other.

In some examples, the mean of the total intensities or of the direct total intensities of all comparable features and the percentage deviation of the individual total intensities or of the direct total intensities from the mean are calculated. This has the advantage of permitting simple and meaningful assessment of the mask.

In another aspect, a mask inspection microscope is provided for characterizing a mask, the mask inspection microscope including a data processing system that performs the methods described above.

The data processing system can be, for example, a computer programmed such that the methods described above are performed.

In some examples, a non-imaging sensor is provided for determining a direct total intensity of an aerial image. This has the advantage of making it possible to determine the direct total intensity of a mask with high precision.

DETAILED DESCRIPTION

Figure 1:
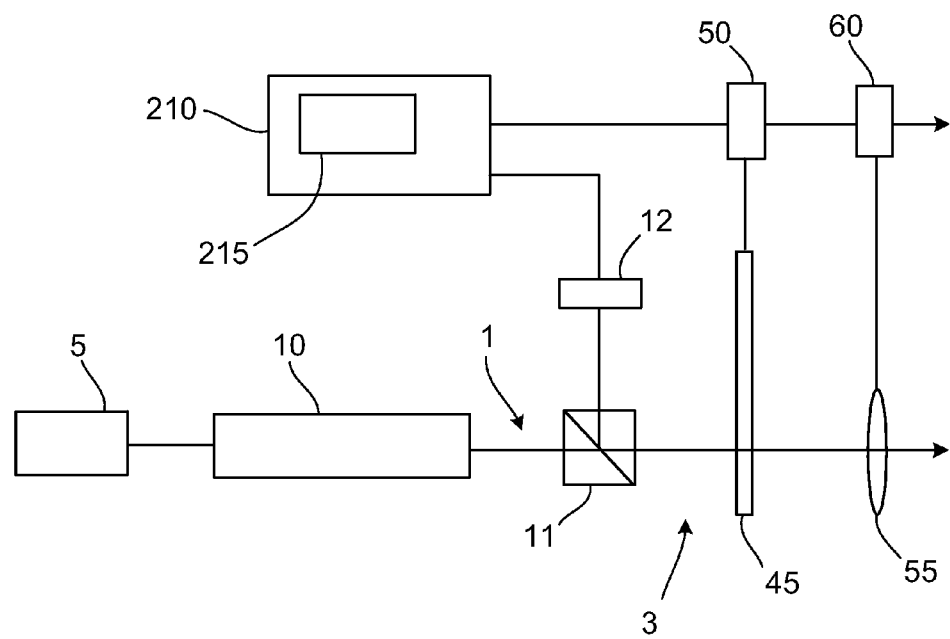
FIG. 1 is a longitudinal section of a portion of an illumination beam path of a mask inspection microscope.

A mask inspection microscope according to a first exemplary embodiment includes, as illustrated in FIG. 1, a radiation source 5, such as an excimer laser that emits illuminating radiation at a wavelength of 193 nm. Next along an optical axis 1 is a homogenizer 10 for homogenizing the intensity distribution of the illuminating radiation in a pupil plane and depolarizing the illuminating radiation. A beam splitter 11 diverts a portion of the illuminating radiation to an energy monitor 12. Time variations of the intensity of the radiation source 5 are recorded by a data processing system 210.

Next is a stop plate 45, which is disposed in a pupil plane of the illumination beam path 3. This serves to configure an illumination setting, such as dipole or annular, for example. A drive 50 provides precise control of the position of the stop plate 45.

Figure 2:
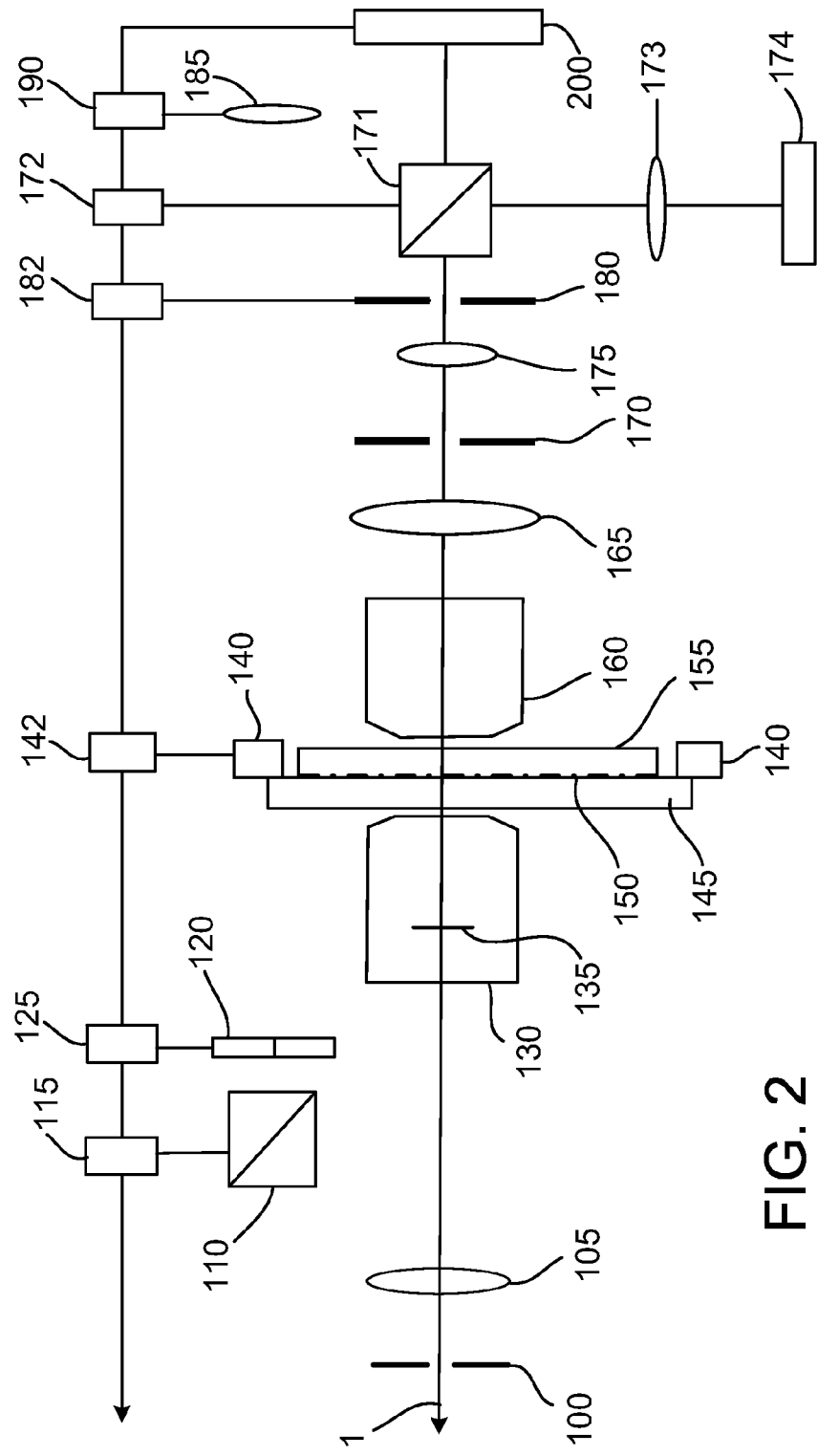
FIG. 2 is a longitudinal section of a portion of an illumination beam path and imaging beam path of a mask inspection microscope.

An adjusted aperture of the stop plate 45 is imaged by a zoom lens 55 with an actuator 60 in the desired size on a resultant pupil plane 135 of a condenser 130, as illustrated in FIG. 2. The imaging scale can be varied by a factor of, e.g., 3.

The continuation of the illumination beam path 3 of the first exemplary embodiment is represented in FIG. 2. The next device is a field stop 100, for defining the size of the illumination field on a mask 145. The field stop 100 is followed by a tube lens 105 and the condenser 130 with the pupil plane 135. The field stop 100 can have a square opening, which can have an edge length of, e.g., 340 µm. On the mask, this results in an image field with an edge length of, e.g., 26 µm.

To polarize the illuminating radiation, polarizers 110 and 120 can be brought into the illumination beam path 3 by drives 115 and 125. The polarizer 110 polarizes the illuminating radiation linearly, and the direction of polarization can be adjusted by using the drive 115 to rotate the polarizer 110. To effect tangential polarization of the illuminating radiation, the polarizer 120, which is embodied as a segmented polarization converter, is brought into the illumination beam path 3 in addition to the polarizer 110. The linear polarization is rotated sectorwise by the polarizer 120 to yield approximately tangential polarization. Three variants of the polarizer 120 are available (not shown in FIG. 2). Division into 4, 8 or 12 sectors can be selected.

The to-be-inspected mask 145 having a feature 150 is protected by a pellicle 155. The mask rests on a mask holder 140, which is moved by a drive 142 laterally in a plane, denoted the xy-plane, in order to move the mask to the desired position such that the segment of the mask of which an aerial image is to be taken is in the illumination beam path 3.

The position of a segment of which an aerial image is being taken is specified by indicating the center of that segment. This position of the center is saved in conjunction with a captured aerial image.

By using the drive 142, the mask is also moved in the direction of the optical axis, the z-axis, to effect focusing. Alternatively, focus is obtained by moving an objective lens 160 in the direction of the optical axis.

To orient the mask in the xy-plane, the planes of best focus at three positions on the mask, preferably in edge regions of the mask, are determined, i.e., the z-coordinates of the respective positions are found. The plane of the mask is specified on the basis of the coordinates of these three positions.

The image of the mask is projected by the objective lens 160 via a tube lens 165, a field stop 170, and a magnification lens 175 to a detector 200, which can be a CCD (charge coupled device) chip. The numerical aperture is adjusted by a NA stop 180 using a drive 182. The variations in the intensity of the illuminating radiation that are registered by the energy monitor 12 are used to correct the intensities of the captured aerial image. The intensities of a captured aerial image thus are largely free of variations in the intensity of the illuminating radiation.

To measure the direct total intensity of an aerial image, after the NA stop 180, a beam splitter 171 is brought into the beam path 3 by using a drive 172, as illustrated in FIG. 2. In a variant not shown in the figure, a mirror can be introduced instead of the beam splitter. It is not possible to use both sensors simultaneously when the mirror is used, however, and all the light intensity is used for the sensor measuring the direct total intensity. The beam deflected by the beam splitter 171 or the mirror then passes through a converging lens 173 to impinge on a high-sensitivity non-imaging sensor 174. The sensor 174 can be, e.g., a photodiode or a photomultiplier, which is known as a PMT (photomultiplier tube). Measurement of the direct total intensity can also be used to correct time variations in the intensity of the illumination radiation.

To image the pupil plane of the illumination beam path 3 on the detector 200, a Bertrand lens 185 is brought into the illumination beam path 3 by a drive 190.

All drives 50, 60, 115, 125, 142, 172, 182, and 190 and detectors 174 and 200 are connected to the data processing system 210 equipped with an input and output unit 215. Control of the mask inspection microscope is effected by using the data processing system 210. It is embodied as a computer programmed in such a way that the methods for characterizing the mask are executed. The data processing system 210 reads the detector 200, causing the particular aerial image to be saved and the image data processed.

In another exemplary embodiment (not shown in the drawings), the mask inspection microscope operates in reflection. Here, the mask 145 is illuminated from the side comprising the feature 150. The mask therefore rests with precisely the opposite side on the mask holder 140. The radiation reflected by the feature 150 is decoupled from the illumination beam path 3 by a beam splitter in a known manner and pursues its course, as illustrated in FIG. 2, until it is imaged on the detector 200.

Figure 3:
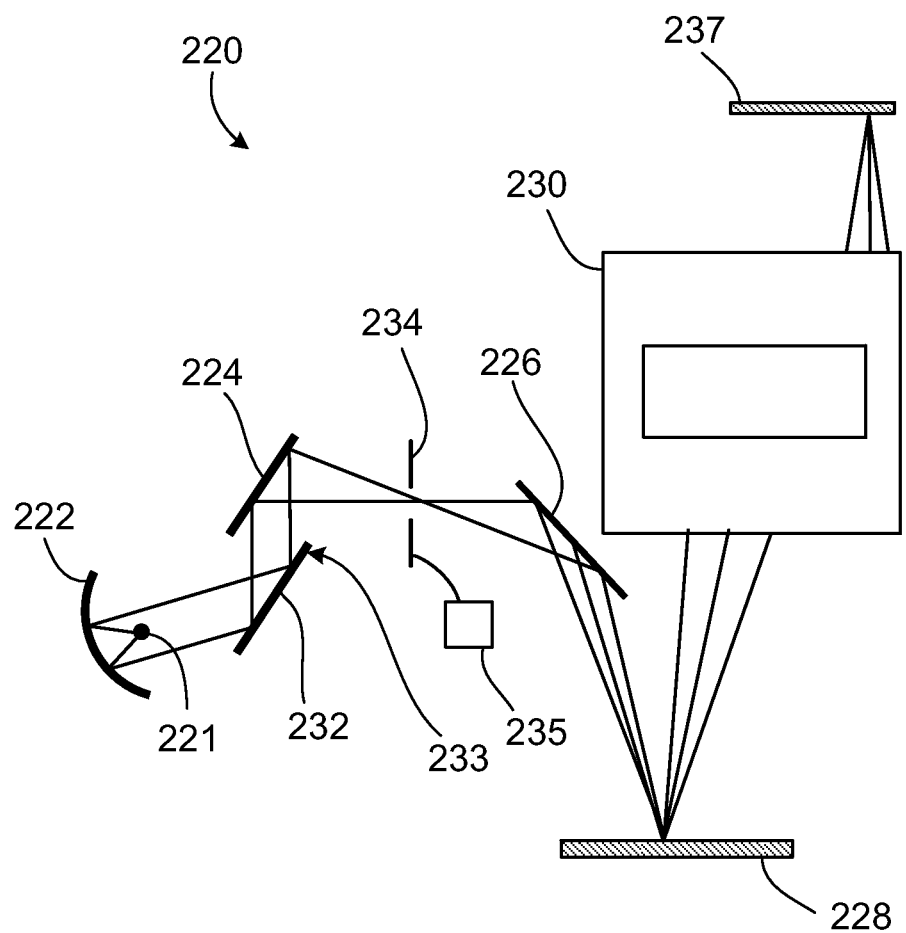
FIG. 3 is a schematic representation of a mask inspection microscope operating with illuminating radiation in the EUV range.

Referring to FIG. 3, in some implementations, a mask inspection microscope 220 is operated with illuminating radiation in the EUV range, having a wavelength of, e.g., 13.5 nm. The radiation from an EUV radiation source 221 is collected by a collector 222 and reflected via mirrors 224 and 226 onto a to-be-inspected EUV mask 228. A field stop 234 serves to determine the size of the illumination field on the EUV mask 228. Stop 234 is imaged on the mask. A drive 235 is used to focus or defocus the image of the stop 234. By means of a stop 232, which is disposed on a stop plate 233 (analogously, for example, to the stop on stop plate 45), the desired illumination angle is obtained. An image of the EUV mask is projected via the imaging system 230 onto a detector 237, which, like drive 235, as well, is connected to a data processing system (not shown) that reads the detector and processes the image data.

Captured aerial images are stored as digital grayscale images in the memory of the data processing system 210. They are in the form of a matrix of 1000×1000 pixels with intensities $I_{n,m}$ represented as values in a range of 0 to 255. The subscripts n and m denote the row and column of a pixel of the detector.

Known methods, such as, for example, Kirchhoff simulation or rigorous methods, are used to simulate aerial images from the mask design. Simulators of this kind are also available commercially, such as, for example, the software Calibre Workbench from Mentor Graphics. Total intensities are determined from regions of simulated aerial images in the same manner as in the case of measured images. Simulated aerial images can be used to compare the measured aerial images or the total intensities to the simulated aerial images. They are also used to correct the position of the captured aerial images relative to the mask design. The illumination settings and polarization settings are also included in the simulation of the aerial images.

To correct the position of a captured aerial image, the captured aerial image is overlaid with a simulated image of the appropriate segment of the subfeature of the mask. For this purpose, the to-be-expected aerial image of the mask segment for measurement is simulated on the basis of the mask design file. For each segment to be measured, the aerial image of the real mask is then aligned with the simulated aerial image using a correlation algorithm, thus permitting more precise position determination. Any deviation of the actual position from the target position of the segment is determined. This deviation, referred to as the position error, is stated as the value pair $\Delta X$ and $\Delta Y$. The measured segment is then shifted appropriately so that the position of the segment corresponds to the specified target position. To achieve this, the X- and Y-coordinates of all the pixels in the segment of the mask are corrected by the position errors $\Delta X$ and $\Delta Y$.

As a correlation algorithm, the differences between the intensity values of the mutually overlaid pixels of the two images are calculated pixel by pixel. The absolute differences between the grayscale values of the individual pixels overlying one another after the particular shift are summed. The images are shifted relative to each other until a minimum of the summed differences is reached.

In this operation, the images are shifted relative to each other pixel by pixel or in smaller units than pixels, i.e., in subpixel increments. Such correlation methods are known, for example, from DE102006059431 and U.S. published application 2010/0104128.

The starting point for the calculation is the position of the aerial image as defined by the target value for the position of the mask holder and the position of the simulated image in the mask design.

To determine the total intensity $I_G$ of a square region of an aerial image, all the intensities $I_{n,m}$, within this region of the aerial image are added together:

$$I_G = \sum_{n1}^{n2} \sum_{m1}^{m2} I_{n,m}$$

The region of the aerial image extends from row n1 to row n2 and column m1 to column m2 of the detector. If the total intensity of the aerial image is being determined, all the intensities of the aerial image are added together.

In a variant of the exemplary embodiment, the total intensities to be determined are normalized (clear normalization). A completely featureless region of the mask is brought into the imaging beam path of the mask inspection microscope. The intensities of the aerial image acquired in this way are used to determine the total intensity. The total intensity thus determined is referred to as the clear intensity $I_{clear}$. To perform the normalization, the total intensities are divided by the clear intensity. The normalized total intensity is: $I_{G\_normalized} = I_G/I_{clear}$. The clear-normalized total intensities are calculated, for example, in order to compare the total intensities of different aerial images with one another. In a further exemplary embodiment, the normalization is performed by measuring the clear intensity $I_{clear}$ without a mask in the beam path.

To normalize the total intensity of one region of an aerial image, the clear intensity of one region is used. If the clear intensity of an entire aerial image is known, the clear intensity of one segment can be calculated on the basis of the size ratios between the region and the aerial image as a whole.

In a variant of the exemplary embodiment, the normalization is performed on the direct total intensity measured by the non-imaging sensor 174. This can be done either against the mask or against the free beam path, analogously to the method described above.

In a variant of the exemplary embodiment, for purposes of calibration the total intensity is determined for one or more comparable features of a mask whose grating periods and line widths are known.

If the grating period is constant, the total intensity depends, in good approximation, exclusively on the line width. By calibration, the absolute values of the line widths can be determined from total intensity measurements.

The calibration can be performed against absolute measurements of the feature on the mask or on the wafer. To measure the absolute dimensions of the line width, both on-mask and on-wafer, a scanning electron microscope is used. Calibration can also be performed against simulated aerial images.

Since only slight deviations of the line width (i.e., of the CD, the critical dimension) from the nominal value are likely with the masks that are to be inspected, a linear relationship between the change in total intensity and the line width can be assumed in good approximation.

In a variant of the exemplary embodiment, the calibration is performed for the direct total intensity.

Figure 4:
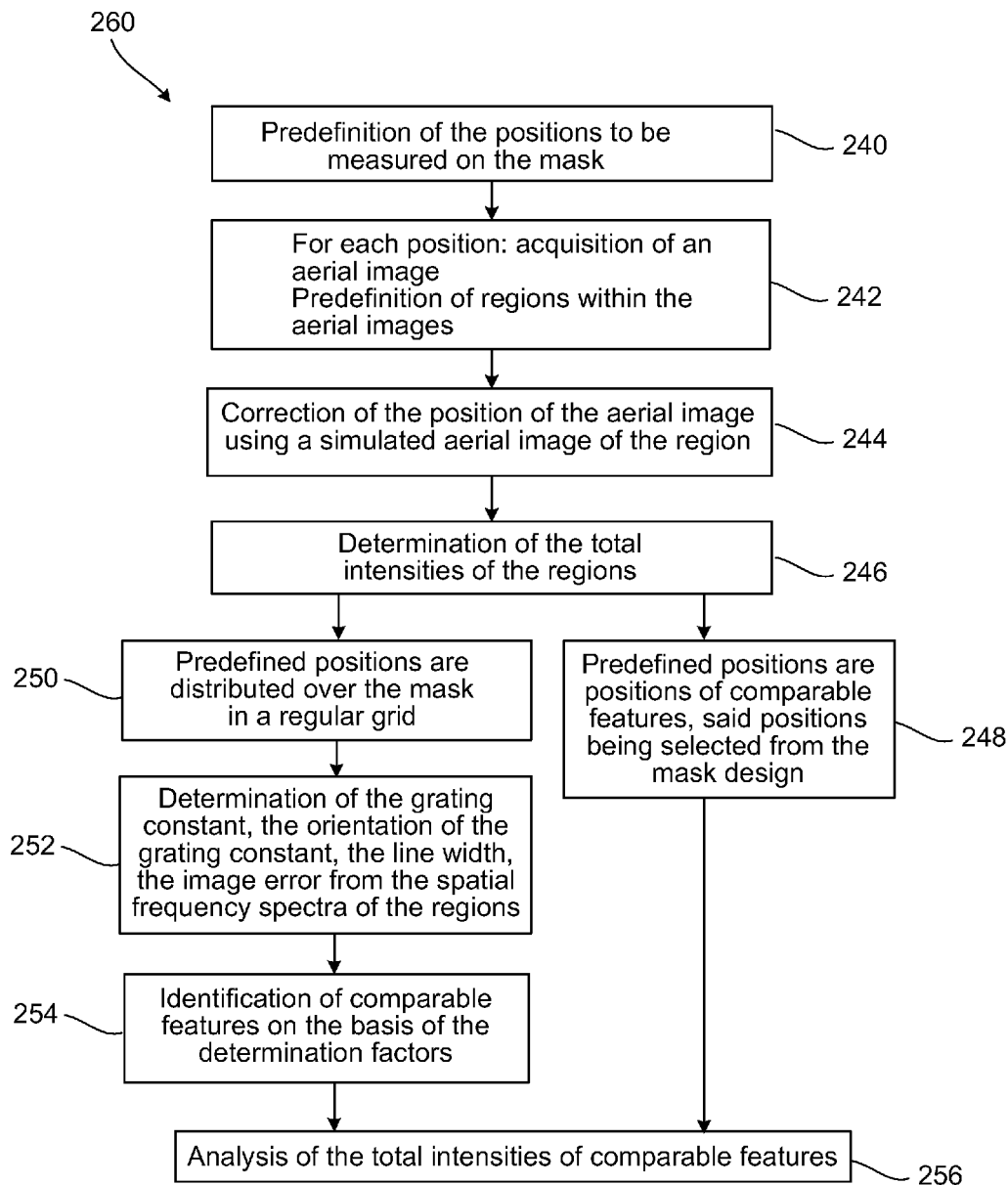
FIG. 4 is a flow chart of an example process.

A flow diagram 260 of an example process for characterizing a mask is provided in FIG. 4. To characterize a mask, first, the desired illumination setting is selected. The positions to be measured on the mask are predefined 240. If the positions on a mask of segments having comparable features are known, total intensities are determined specifically at those positions. The positions of comparable features can be determined, for example, from the mask design, i.e., from the information regarding features formed on the mask.

For each position to be measured, an aerial image is acquired, and regions within the aerial images are predefined 242. The region or regions of an aerial image that are to be included in the determination of the total intensity can be predefined using, e.g., the input and output unit 215 of the data processing system 210. The position of the center of each region is stored in a storage device.

The position of the aerial image is corrected using a simulated aerial image of the region 244. The total intensities of the regions are determined 246.

If the mask design, i.e., the feature formed on the mask, is known, the predefined measurement positions are positions where comparable features can be found, in which the positions are selected from the mask design 248. The total intensities of the regions of the measured positions can also be determined from the simulated aerial images, as noted above. To perform the analysis, the measured total intensities are compared to the simulated total intensities. The percentage deviations can be illustrated graphically, as stated below.

In some implementations, if the mask design is not predefined, positions evenly distributed over the mask are specified for measurement 250. For example, positions are specified that are disposed in a grid laid over the mask as a matrix of, for example, 1000×1000 positions.

The grating period, the line width and orientation of the grating, the clear-normalized total intensities and image errors are determined from the spatial frequency spectra of the regions 252. Comparable features are identified based on the basis of certain determination factors 254. The total intensities of comparable features are analyzed 256.

In some implementations, comparable features are selected from all the regions of the captured aerial images, based on criteria that include, e.g., the grating period, the line width and orientation of the grating period, the clear-normalized total intensities and the image errors determined above. These criteria can be applied individually or in combination.

In the analysis of the total intensities of comparable features, the clear-normalized intensities are determined from all of the total intensities. Clear-normalized total intensities that fall within a predefined tolerance range are combined into groups of comparable features. A tolerance range within a group is predefined. Total intensities having values outside the tolerance range are not included in the characterization of the mask.

The groups formed in this way can be analyzed further. The grating periods and the line widths are determined by frequency analysis of the aerial images. The grating period and the line width are determined by analyzing the spatial frequency spectrum. To perform the frequency analysis, the aerial image is transformed from the position-space to the Fourier space, i.e., the spatial frequency spectrum is calculated. The frequencies of the diffraction orders of the grating periods appear in the spatial frequency spectrum as sharp maxima. The grating periods can be calculated by determining the positions of these maxima in comparison to the positions of the maxima of the frequency of the zero$^{th}$ diffraction order. The frequency analysis has low requirements in terms of image definition, so no precise focusing need be done when taking the aerial images.

Frequency analysis of the aerial images also reveals image errors. If an aerial image or a predefined region, for example, consists only in part of lines and spaces, and also, in part, for example, of an array of pinholes, the total intensity of that region is not comparable to the total intensity of a region of an aerial image of a feature exclusively made up of lines and spaces. Aerial images or regions in which image errors are found are not included in any further characterization. Alternatively, the region of the aerial image included in the analysis is changed. In the example cited here (an aerial image composed of lines and spaces but also consisting in part of an array of pinholes), additional maxima occur in the spatial frequency spectrum. These can be detected. If these maxima exceed a predefined threshold value, the image is excluded from the evaluation.

For rapid analysis of the aerial images or regions, in a variant, spatial frequency spectra are determined for features commonly encountered on masks. These can be calculated not only from measured aerial images, but also from simulated ones. The positions and heights of the maxima are then stored in a database. Thus, the particular feature can be quickly inferred from the positions and heights of maxima in the spatial frequency spectra of measured images. The position of such a maximum is determined by the grating period. The intensity of such a maximum is determined by the width of the lines and by material parameters of the mask, such as thickness and refractive index, and illumination parameters, such as, for example, wavelength, illumination setting or polarization.

To the extent that the total intensities were, as noted above, calibrated against known CD values, the absolute CD values can be indicated as a function of position on the mask in a two-dimensional diagram.

In a variant of the analysis, for a group of comparable features, the percentage deviation of all the values of the total intensity from its mean is calculated. Different percentage deviations are assigned different colors or color shades. The measurement values are then represented by the respective color in a two-dimensional diagram of the mask. A nominal value for the critical dimension of a mask that is to be inspected is usually known. In analyzing the measured total intensities of a mask, it can be assumed that this critical dimension is approximately equal to the mean of the total intensities of comparable features. The relative deviation of the total intensities from the mean then corresponds to the relative deviation from the predefined critical dimension.

A variant of the exemplary embodiment is used in the case of masks having numerous regions with identical features, referred to as dies. To increase the precision of the analyses described above, the average of the total intensities of identical positions on all the dies is measured. Then, to perform the analysis, the percentage deviation of the individual intensity quotients from the average value across all the dies is stated for each position.

The features described above related to processing of data can be implemented in digital electronic circuitry, or in computer hardware, firmware, software, or in combinations of them. The features can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. Alternatively or addition, the program instructions can be encoded on a propagated signal that is an artificially generated signal, e.g., a machine-generated electrical, optical, or electromagnetic signal, that is generated to encode information for transmission to suitable receiver apparatus for execution by a programmable processor.

A number of implementations have been described. Nevertheless, it will be understood that various modifications may be made. For example, elements of one or more implementations may be combined, deleted, modified, or supplemented to form further implementations. As yet another example, the logic flow depicted in FIG. 4 does not require the particular order shown, or sequential order, to achieve desirable results. In addition, other steps may be provided, or steps may be eliminated, from the described flow, and other components may be added to, or removed from, the described systems. Accordingly, other implementations are within the scope of the following claims.

What is claimed is:

1. A method for characterizing a mask having a feature, comprising:
   generating an aerial image of at least one segment of a feature of a mask,
   acquiring a spatially resolved intensity distribution of the aerial image,
   calculating a total intensity value from the sum of the intensities of a plurality of pixels of at least one region of the aerial image, and
   determining a characteristic of the at least one segment of the feature of the mask based on the total intensity value.

2. The method of claim 1, wherein the total intensity value is normalized to a reference quantity.

3. The method of claim 2 in which the reference quantity comprises the total intensity measured on a featureless mask.

4. The method of claim 2, comprising determining a clear intensity value from intensities of an aerial image of a featureless mask region, wherein normalizing the total intensity value comprises dividing the total intensity value by the clear intensity value.

5. The method of claim 1,
   wherein determining a characteristic of the at least one segment of the feature of the mask comprises determining a line width of the feature of the region on the basis of a correlation between at least one determined total intensity of a feature and a known line width of the feature.

6. The method of claim 1, comprising:
   predefining at least one position on the mask at which the mask will be characterized.

7. The method of claim 1, wherein a plurality of positions evenly distributed over the surface of the mask are predefined.

8. The method of claim 1, wherein positions on the mask at which comparable features are formed on the mask are determined.

9. The method of claim 1, comprising:
   analyzing the aerial images to identify positions having comparable features.

10. The method of claim 1, comprising: determining at least one of the following factors on the basis of the aerial images: grating constant, orientation of the grating, line width, and image error.

11. The method of claim 1, wherein an exact position is determined by comparing at least one region of the captured aerial image to a simulated aerial image.

12. The method of claim 1, wherein a direct total intensity is determined by acquiring an individual intensity by using a high-sensitivity non-imaging sensor.

13. The method of claim 1, wherein a mean of the total intensities or of the direct total intensities of all comparable features and the percentage deviation of the individual total intensities or direct total intensities from the mean are calculated.

14. The method of claim 1 in which the total intensity value is a single value.

15. A mask inspection microscope for characterizing a mask, comprising a data processing system that is configured to:
   generate an aerial image of at least one segment of a feature of the mask,
   acquire a spatially resolved intensity distribution of the aerial image,
   determine a total intensity value from the sum of the intensities of a plurality of pixels of at least one region of the aerial image, and
   determine a characteristic of at least one segment of a feature of the mask based on the total intensity value.

16. The mask inspection microscope of claim 15, comprising a non-imaging sensor for determining a direct total intensity of an aerial image.

17. The mask inspection microscope of claim 15 in which the data processing system is configured to normalize the total intensity value to a reference quantity.

18. The mask inspection microscope of claim 17, comprising determining a clear intensity value from intensities of an aerial image of a featureless mask region, wherein normalize the total intensity value comprises dividing the total intensity value by the clear intensity value.

19. The mask inspection microscope of claim 15 in which the data processing system is configured to determine a line width of the feature of the region on the basis of a correlation between at least one determined total intensity of a feature and a known line width of the feature.

20. The mask inspection microscope of claim 15 in which the data processing system is configured to compare at least one region of the captured aerial image to a simulated aerial image.

21. The mask inspection microscope of claim 15, comprising a high-sensitivity non-imaging sensor to sense individual intensities for use in determining the total intensity.

22. The mask inspection microscope of claim 15, in which the total intensity value is a single value.

23. A method of determining a critical dimension distribution on a mask, the method comprising:
   generating a plurality of aerial images of a mask, each aerial image representing a portion of the mask, the portion having a feature, each image having pixels that have intensity values;
   for each aerial image, calculating a total intensity value of the aerial image from the sum of the intensities of a plurality of pixels of the aerial image;
   for each aerial image, determining a critical dimension value based on the total intensity value and a correlation between predetermined total intensities of features and known critical dimension values; and
   determining a distribution of critical dimension values on the mask.

24. The method of claim 23, comprising normalizing the total intensity value of each aerial image according to a total intensity measured on a featureless mask.

25. The method of claim 23 in which the total intensity value is a single value.

26. A method for characterizing a mask having a feature, comprising:
- generating an aerial image of at least one segment of a feature of a mask,
- acquiring a spatially resolved intensity distribution of the aerial image,
- calculating a total intensity value from the intensities of at least one region of the aerial image,
- determining a characteristic of the at least one segment of the feature of the mask based on the total intensity value;
- determining a clear intensity value from intensities of an aerial image of a featureless mask region,
- wherein the total intensity value is normalized to a reference quantity, including dividing the total intensity value by the clear intensity value.

27. A mask inspection microscope for characterizing a mask, comprising a data processing system that is configured to:
- generate an aerial image of at least one segment of a feature of the mask,
- acquire a spatially resolved intensity distribution of the aerial image,
- determine a total intensity value from the intensities of at least one region of the aerial image,
- determine a characteristic of at least one segment of a feature of the mask based on the total intensity value,
- determining a clear intensity value from intensities of an aerial image of a featureless mask region, and
- normalize the total intensity value to a reference quantity, including dividing the total intensity value by the clear intensity value.

* * * * *